United States Patent [19]

Brown

[11] 4,357,716

[45] Nov. 9, 1982

[54] DEVICE AND METHOD FOR CEMENTING A HIP PROSTHESIS IN A FEMORAL CANAL

[76] Inventor: Byron L. Brown, 2315 Hendricks, Ft. Smith, Ark. 72903

[21] Appl. No.: 218,763

[22] Filed: Dec. 22, 1980

Related U.S. Application Data

[63] Continuation-in-part of Ser. No. 167,070, Jul. 9, 1980, abandoned.

[51] Int. Cl.³ .......................... A61F 1/00; A61F 1/24
[52] U.S. Cl. ........................................ 3/1.913; 3/1.91; 128/92 CA
[58] Field of Search ................................ 3/1.9–1.913; 128/92 C, 92 CA

[56] References Cited

U.S. PATENT DOCUMENTS

| 4,068,324 | 1/1978 | Townley et al. | 3/1.913 |
| 4,266,303 | 5/1981 | Park | 3/1.91 |
| 4,274,163 | 6/1981 | Malcom et al. | 3/1.91 |

FOREIGN PATENT DOCUMENTS 2555717  6/1977  Fed. Rep. of Germany ....... 3/1.912

Primary Examiner—Ronald L. Frinks
Attorney, Agent, or Firm—Sigalos & Levine

[57] ABSTRACT

A device for cementing a femoral stem hip prosthesis having a head, neck, collar and stem in a femoral canal comprising means for mounting a femoral stem of the prosthesis in the femoral canal in a rigid relationship thereto, and means for cementing the prosthesis stem in the canal while in the rigid relationship whereby a strong bond is obtained between the prosthesis stem and the femur.

34 Claims, 21 Drawing Figures

DEVICE AND METHOD FOR CEMENTING A HIP PROSTHESIS IN A FEMORAL CANAL

This application is a continuation-in-part of Application Ser. No. 167,070, filed July 9, 1980, and now abandoned.

BACKGROUND OF THE INVENTION

The present invention relates to a method and apparatus for mounting a femoral stem hip prosthesis in a femoral canal with the use of a cement. It is well known in the prior art to initiate total hip replacement in individuals where: (1) a painful and/or severely disabled joint results from osteo arthritis, traumatic arthritis, or rheumatoid arthritis; (2) there is an occurrence of persistent or recurrent pain and/or physical impairment subsequent to femoral head replacement, cup arthroplasty, or other conventional techniques; (3) difficult clinical management problems occur where experience has indicated that more conventional arthroplasty techniques are not likely to achieve satisfactory results or where arthrodesis is contra-indicated because of age, sex, occupation, or height of the patient, or (4) bone stock is of poor quality of inadequate for other reconstruction techniques as indicated by deficiencies of the femoral head, neck or acetabulum. The femoral stem hip prosthesis is not confined to the replacement of total hips. Some patients need only the femoral head and neck to be replaced. In these cases, the head of the femoral prosthesis is inserted into the patient's existing acetabulum. In this type of prosthesis, the stem may or may not be cemented in. The most commonly used prosthesis of this type are the Thompson and Moore unfenestrated prostheses.

Where total hip replacement is required, the patient's hip socket, the acetabulum, and the femur just be prepared to receive mating components. The acetabulum is modified to receive an acetabular cup which mates with the head of the femoral stem prosthesis which is attached to the femur.

In order to prepare the femur for the insertion of the femoral stem prosthesis, the proximal end of the femur is prepared by retracting the muscle at the greater trochanter laterally and freeing any soft tissue which might be present. After the proximal end of the femur is exposed, the head and neck is then resected with a reciprocating saw in a 5° to 10° anteverted plane or as medically indicated and obliquely from the base of the neck laterally to the base of the head medially so that the angle of the cut approximates the angle of the prosthetic platform. The femur is then prepared by rasping or curetting the intramedullary canal in its proximal end and extending this process well laterally and distally in the proximal shaft to accommodate a cement mass for support and fixation of a stem of a femoral prosthesis. Once the canal has been properly prepared by reaming and curettage, the distal canal is plugged, utilizing a bone plug obtained from the femoral head. An alternate method of plugging the canal utilizes a bolus of acrylic cement in the "rubbery" elastic stage just prior to setting and tamping the plug down distally 2 cm. below the stem tip. In both cases, the plugs effectively seal off the canal to prevent excessive penetration of cement below the stem prosthesis tip. The femoral canal is then dried and the acrylic cement is mixed and poured into a syringe and immediately injected into the dried femoral canal from distal to proximal. A rubber dental dam may be stretched over the proximal femur and the acrylic digitally finger packed. After the acrylic has reached the dough stage, the dam may be removed and additional finger packing is vigorously performed for at least a minute to two minutes to insure adequate filling and penetration.

After the cement has been packed into the proximal femur, the femoral prosthesis is carefully inserted to avoid varus placement. When the acrylic has reached the late dough stage, the stem of the prosthesis is inserted into the femoral canal and either held by hand or by the use of an inserter; the prosthesis is carefully held in place during the final stages of setting or hardening of the acrylic. Present state of the art requires the femoral stem prosthesis to be held in its desired position manually for approximately six to twelve minutes while the cement hardens. Two types of holders or drivers presently used are Zimmers #4044-23 Driver or Zimmers 4046-10 Femoral Prosthesis Holder. Either of these two requires the operating surgeon to hold steady the femoral head with constant and non-pulsating pressure for six to twelve minutes. This is humanly impossible and when the cement has hardened, there are varying degrees of looseness of the cement about the prosthesis. When the patient begins walking and the prosthesis becomes weight bearing, it is possible that the femoral stem and cement become loose and may require re-cementing. In still other instances, the metal femoral stem of the prosthesis may break in the region of the middle third of the metal stem. This occurs because the distal third of the metal stem is held securely but the proximal position is loose and when weight is applied, the force is too great and the metal breaks.

Further, there has recently been introduced the Miller Cement Delivery System by Zimmer and the Exeter Pressurized System by Howmedica which temporarily pressurizes the cement into the lower part of the femoral bone canal by use of an inflated balloon or rubber plug. This pressure is released when the plug or balloon is removed so that the prosthesis can be inserted in the femoral canal. The proximal portion of the femoral bone canal is then packed with cement digitally by pushing the cement into the canal and about the prosthesis with the fingers. The problem, of course, is that the pressure is released when the prosthesis is inserted and, again, the prosthesis must be hand-held until the cement hardens.

Further, in the present state of the art, it is the practice of the surgeon to insert the femoral stem prosthesis into the femoral canal and observe or "eyeball" the overall anticipated position and placement of the prosthesis. He attempts to place the distal end of the femoral stem medially in the femoral canal rather than laterally. Finally, a decision is made to determine that the position is satisfactory and the surgeon proceeds to place the cement into the femoral canal and hold the prosthesis manually in the same previous "eyeballed" position until the cement hardens. At a later time, perhaps hours or days after the surgery, an X-ray is taken which may reveal the distal end to be more laterally positioned than was supposed at the trial insertion during surgery. The surgeon may not have recognized the slight shift of the stem of the prosthesis while inserting it into the cemented femoral canal. Further, the surgeon may only assume that the prosthesis collar abuts the femur calcar as he inserts the prosthesis into the cemented canal. Also, the failure to insert the prosthesis to exactly the same depth as during the trial position may occur.

Also, the positioning of the head and neck of the prosthesis in anteversion, a relationship of the head and neck of the prosthesis with the shaft of the femur, may not be ascertained accurately by "eyeballing". Thus, positioning of the prosthesis in varying degrees of valgus or varus is important and is related in part to the position of the distal end of the femoral stem. It is also related to the position of the proximal end of the prosthesis stem in the intertrochanteric area.

A variety of changes of position may occur from the "eyeballing" position to the cemented position but cannot be determined or fully evaluated until the cement has hardened. At that time, of course, the task of removing the prosthesis and cement is a major additional operation if undertaken.

Also, the surgeon must presently pack the cement beneath the collar of the prosthesis and about the bone calcar with the fingers, and it is nearly impossible to do it accurately with this method.

Finally, the bone reacts to the stress and strains that are placed upon it. Thus, it builds a stronger, thicker cortex where the stress is greater and weaker, thinner cortex where the stress is less. Anatomically, the cortex is thicker at the calcar and on down the anteromedial aspect of the shaft of the femur. This is so because this segment of bone bears most of the weight and stress in walking, running and climbing steps. Presently, it is a chore of varying skill on the part of the surgeon to cover well the cut surface of the calcar or the cut surface of the anteromedial aspect of the femur. When the cut surface of the cortex is not capped with cement, the resultant load on the femoral stem prosthesis is transmitted down the canal of the femur. When load pressure is applied to the prosthesis and cement, if the cortex is not capped with cement, the effect is to wedge the cement into the femoral canal. This occurs because the proximal end of the femoral bone canal is greater in circumference than is the bone canal at the junction of the proximal and middle third of the femoral bone canal. This wedged pressure exerts outward pressure on the cortex in addition to the longitudinal pressure from the weight of the individual. When the cut end of the femur is not capped with cement, the resultant forces are not natural or physiological and, in some instance, wasting away of the calcar and the anteromedial aspect of the femoral shaft is seen by X-rays months later due to atrophy or disuse.

Thus it is an object of the present invention to provide constant pressurization on the cement during the hardening of the cement and a fixed jig which holds the prosthesis in a fixed relationship to the femur, thus eliminating all motion of the prosthesis while the cement is hardening. Further, the constant pressurizing of the cement produces packed cement in the femoral canal and about the entire length of the prosthesis stem so that the pressure is applied higher on the metal stem and more evenly on the entire metal stem with a weight load pressure being applied on a much shorter lever arm and thus having less possibility of breaking the metal stem. Further, pressurizing the cement in the canal during hardening will decrease loosening of the cement-stem unit. Thus, the present invention obviates the strain placed upon the surgeon while holding the impacter, and thus the prosthesis, motionless for approximately six to twelve minutes.

It is still another object of the present invention to provide a device which allows constant pressurized cement to fill the femoral canal while the cement is hardening, thus securely engaging the steam prosthesis.

Further, the present invention allows the femoral stem prosthesis to be placed in position prior to applying cement and the position of the stem, the position of the collar on the calcar, the length of the neck, the anteversion and the varus or valgus to be determined by X-ray. If any of these positions are not satisfactory, the stem prosthesis can be repositioned to correct these factors and held rigidly in the new position while being X-rayed again to determine the final position in which the prosthesis will rest when secured with cement.

Also, the use of the constantly pressurized cement not only packs the cement under the collar of the prosthesis, but maintains pressure on the cement in this area as well as the entire cement mass while it hardens. Finally, the present invention which utilizes a constantly pressurized cement causes the calcar and approximately the medial ⅔rd of the cut surface of the femur to be capped with the cement.

This enables the weight load of the person to be transmitted to the cortex of the femur as well as the cement. The other forces of stress and strain and torgue are transmitted to and through the cement as nearly normal as presently possible to simulate the medullary trabeculae.

Some surgeons use a collarless femoral stem prosthesis and operate on the theory that it is not necessary to cover the cut surface of the femur with cement. This group of surgeons believes that if the cement is inserted well into the proximal femur that, with the patient's weight bearing, the femoral stem and cement will wedge tightly into the femoral canal if "settling" of the prosthesis occurs or if bone absorption occurs. A recent collarless femoral stem prosthesis is De Puy's Dual-Locking.

SUMMARY

Thus the present invention relates to a device for cementing a femoral stem hip prosthesis having a head, neck, collar, and stem in a femoral canal comprising means for mounting said femoral stem of said prosthesis in said femoral canal in a rigid relationship thereto, and means for cementing said prosthesis stem in said canal while in said rigid relationship whereby a strong bond is obtained between said prosthesis stem and said femur.

The device further includes means for applying said cement to said femoral canal under pressure and means for maintaining said pressure until said cement hardens about said prosthesis stem.

The invention also relates to a method of cementing a femoral stem hip prosthesis in a prepared femoral canal, said prosthesis having a head, neck, collar and a stem, said method comprising of steps of inserting the stem of said prosthesis in said prepared femoral canal, attaching said prosthesis to said femur in a rigid relationship, and cementing said prosthesis stem in said canal while said prosthesis is maintained in said rigid relationship.

The invention also relates to a method including the steps of applying said cement to said prepared femoral canal under pressure and maintaining said pressure until said cement is hardened about said prosthesis stem.

The invention also relates to a method similar to that already mentioned above but for use in the cementing of femoral stem hip prostheses which do not have a collar.

BRIEF DESCRIPTION OF THE DRAWINGS

These and other objects and advantages of the present invention will be disclosed in the course of the following specification, reference being had to the accompanying drawings, in which.

DETAILED DESCRIPTION OF THE DRAWINGS

Figure 1:
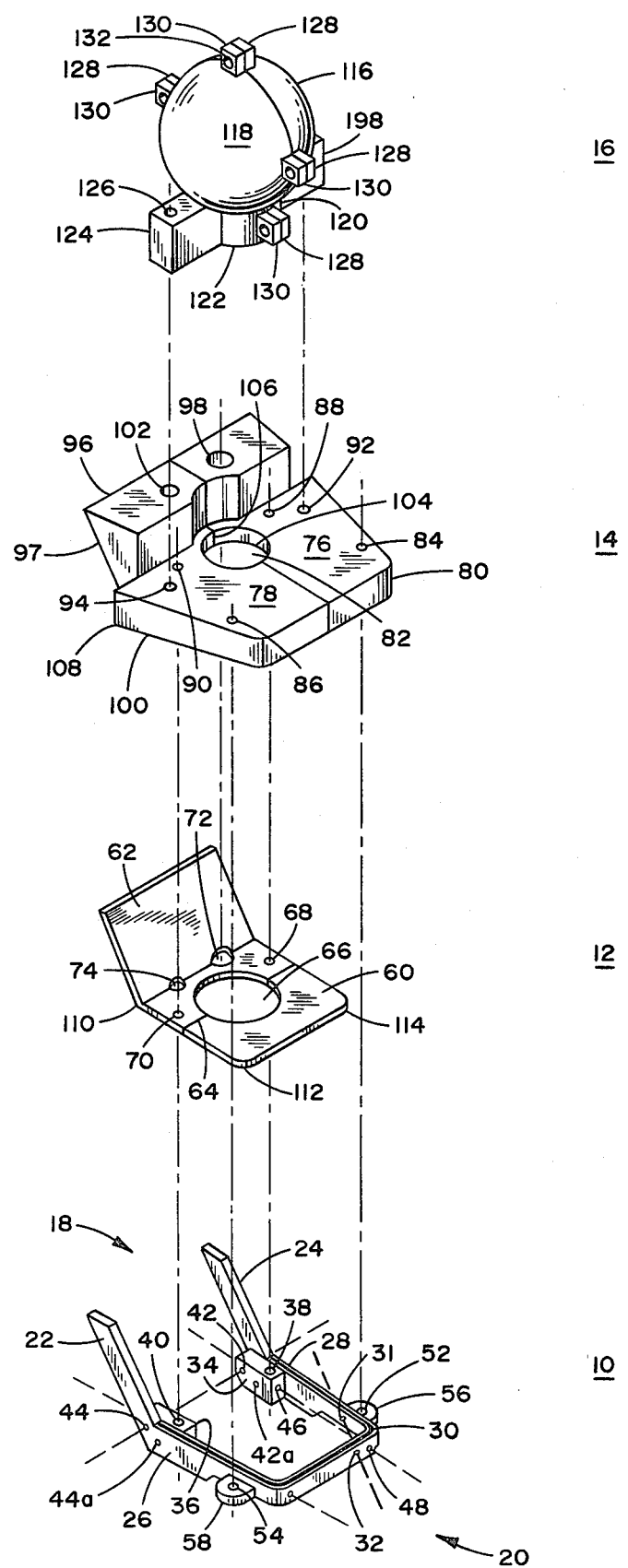
FIG. 1 is an exploded view of the components of the device of the present invention which enables the stem prosthesis to be held in a rigid relationship with the femur while its correct position is being determined and which enables the cement to be applied to said femoral canal under pressure and the pressure maintained while the cement is hardening.

The device of the present invention which is utilized to hold the stem prosthesis in a fixed relationship in the prepared femoral canal while a determination can be made by X-ray of the proper position thereof, and to enable the cement to be applied to the femoral canal under pressure with said pressure being maintained while said cement is drying is shown in exploded view in FIG. 1. The device comprises a base guide 10, a separator-sealer 12, a ceiling 14, and a lid clamp 16.

Base guide 10 is generally U-shaped with the open end 18 of said U being wider than the closed end 20. Wings 22 and 24 extend upwardly and outwardly from the outer end of each arm 26 and 28, respectively. A groove 30 is formed on the upper side of said arms 26 and 28 and in said closed end 20. This groove serves to receive a corresponding flange (shown in FIG. 7) on the bottom of ceiling 14 in order to form a tight seal. Further, in the arm 28 is an orifice 31 which is in alignment with an orifice 32 in closed end 20. These orifices are utilized for a pin to be driven through the cortex of the femur in order to hold the base guide 10 in a rigid relationship thereto.

Further, a support 34 is integrally formed with and/or attached to the inside of wing 24 and arm 28. A similar support 36 is integrally formed with and/or attached to the inside of wing 22 and arm 26. An orifice 38 in the top of support 34 and a similar orifice 40 in the top of support 36 are formed with screw threads or other means to enable the ceiling 14 to be rigidly attached thereto. Also, an orifice 42 in support 34 is in alignment with an orifice 44 in wing 22 as well as orifices, not shown, in support 36 and wing 24 which enable a pin to pass therethrough and through the cortex of the femur to assist in maintaining the base guide in a fixed relationship with respect to said femur while the neck and head of said femur are being resected and the stem prosthesis inserted. Also, an orifice 46 extends longitudinally and horizontally through said support 38 and is in alignment with an orifice 48 in the closed end 20 of said base guide 10 for the purpose of inserting a pin therethrough. The purpose of the pin will be disclosed in detail hereinafter. A like orifice (not shown) is located in support 36 and is in alignment with orifice 50 in closed end 20 of base guide 10. Again, a pin may be inserted through these orifices for a purpose which will be disclosed in detail hereinafter.

Finally, threaded orifices 52 and 54 are located in support 56 and 58, respectively, to receive bolts or other attaching means from ceiling 14 in order to hold the ceiling 14 in a close, cement-tight relationship with base guide 10.

The separator-sealer 12 is comprised of two halves, 60 and 62, separated transversely at line 64 which bisects orifice 66. Orifice 66 fits over and around the collar of the prosthesis. The superior or upper surface of orifice 66 is nearly a circle, but its deeper portions 178 slope to conform to the neck and a portion of the superior or upper surface of the collar of the prosthesis if the prosthesis has a collar (see FIG. 6). Some of them do not. By making the separator-sealer 12 in two halves, the unit can be easily placed around and over the collar of the prosthesis. Orifices 68 and 70 allow bolts or other attaching means from ceiling 14 to pass therethrough to attach to base guide 10. Orifice 72 enables the cement from ceiling unit 14 to pass therethrough into the femoral canal. Orifice 74 is a venting orifice through which the air in the femoral canal being displaced by the cement can escape. The two pieces 60 and 62 coinsist of a plastic, preferable ⅛ inch thick, usually a rubbery material, such as commercially available Polyform or Isoprene, with a layer of a non-toxic absorbable material 177 (see FIG. 6), such as absorbable gelatin (Gelfoam) and the like, ironed onto the bottom thereof; or the separator-sealer may be made of silicone material such as Silastic (Dow Corning) and the use of the word "plastic" herein is inclusive of any of these materials. As stated, sealer 12 fits about the neck and collar junction of the prosthesis and, thus, orifice 66 may be elliptical in shape. Several sets of separator-sealers may be provided and may vary from one another by having a different diameter of the major axis of orifices 66. By selecting a separator-sealer having an orifice with a different diameter of the major axis, one can select a varying degree of anteversion of the head and neck of the stem prosthesis.

The ceiling 14 is also constructed in two halves 76 and 78 along line 106 to enable the unit to be easily placed around and over the neck and collar of the prosthesis. The anterior portion 80 of ceiling 14 is of the same shape as but larger than the generally U-shaped portion of the base guide 10. It has therein an orifice 82 through which the neck of the femoral stem prosthesis may project. It also has therein orifices 84 and 86 through which bolts or other attaching means may extend to fasten ceiling 14 to base guide 10 by means of orifices 52 and 54 in base guide 10. In like manner, orifices 88 and 90 enable bolts or other attaching means to extend therethrough to orifices 38 and 40 of base guide 10 to attach the ceiling 14 thereto in a rigid relationship. Orifices 92 and 94 are threaded to enable lid clamp 16 to be attached thereto by bolts or other attaching means. Quick disconnects of the various types well known in the art may be used instead of bolts if desired.

The posterior area 96 of ceiling 14 rises to a higher level above the anterior portion 80. This elevated posterior portion 96 has two orifices. One orifice 98 is ⅜ inch in diameter and is directed downwardly through ceiling 14 but is also directed anteriorly at such a degree that the opening on the inferior aspect or bottom of the ceiling is at the junction of the sloped surface 97 of posterior 96 and the level or horizontal surface 100 of the anterior or forward portion 80 of ceiling 14. The ⅜ inch orifice 98 is threaded and is utilized to recieve the adapter attachment (shown in (FIG. 5D) for the cement syringe. Orifice 102 is ¼ inch in diameter and also slopes anteriorly. It is threaded at its superior or upper portion for insertion of a pressure plug. The inferior or bottom surface 97 of the posterior half 96 of ceiling 14 is smooth and forms approximately a 41° angle with the level surface 100 of the anterior or forward portion of the ceiling. The angle chosen is the same, referring to FIG. 1, for base guide 10, separator-sealer 12, and the ceiling 14. In addition, the inferior or bottom surface 100 of the anterior or forward porton 80 of ceiling 14 has a ridge or flange 194 near the periphery which meshes or fits into the groove 30 of base guide 10. This can be seen more clearly in FIG. 7.

The inferior or bottom surface 104 of the anterior portion 80 of ceiling 14 is slightly sloped downwardly from the anterior end 80 to the junction 108 of the elevated posterior portion 96 of ceiling 14 so that when the separator-sealer 12 is secured in place, point 110 of the separator-sealer 12 is in contact with the cortex (bone) of the femur, but points 112 and 114 are approximately ⅛ inch above the cut surface or cortex of the femoral bone. This permits the cement, when under pressure, to fill in the space around the neck and collar of the prosthesis and onto the calcar of the resected femur.

Lid clamp 16 also consists of two half shells 116 and 118 for surrounding the head of the femoral prosthesis and also includes two half columns 120 and 122 for surrounding the neck of the prosthesis. A shoulder 124 is attached to column 122 while a second shoulder 198 is integrally formed with and/or attached to column 120. Thus, the two halves 116 and 118 of lid clamp 16 are secured to ceiling 14 by means of bolts or other attachments passing through the orifices in the shoulders, such as orifice 126 in shoulder 124, to corresponding orifices 94 and 92 in ceiling 14. In addition, projections 128 and 130 at the top of half shells 116 and 118 have orifices such as 132 through which a bolt or other like attachment means (including quick disconnect devices) may be inserted to hold the two half shells together. Obviously, as many fastening means, such as projections 128 and 130, may be used as necessary to maintain the lid clamp 16 together as a unit.

Figure 2:
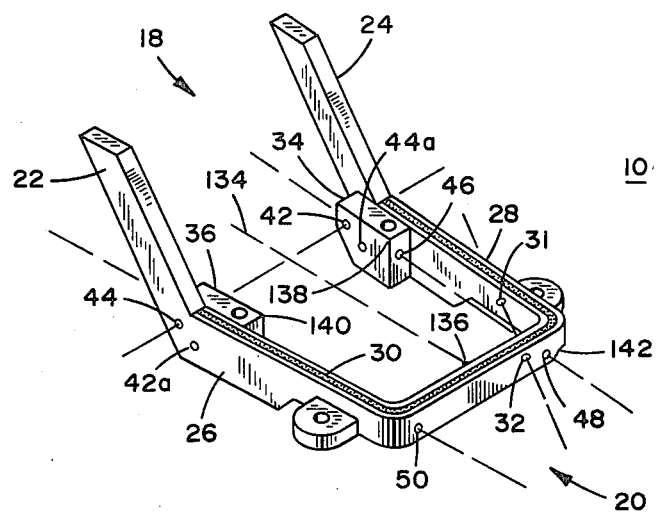
FIG. 2 is an isometric view of the base guide which is rigidly attached to the femur and which enables the surgeon to determine the proper angle at which to resect the head and neck of the femur.

Base guide 10 is shown in an isometric view in FIG. 2. In order for base guide 10 to e used on all sizes of femurs, it may be made in varying sizes. However, if desired, front portion 20 could be split and the split portion slidably connected in a well known manner to make the guide 10 variable in width. In like manner, arms 26 and 28 could be split and slidably interconnected in a well known manner to make the guide 10 variable in length. Guide 10 also must have a left, as well as a right, construction except when a collarless type prosthesis is used. Further, the lid clamp 16, ceiling 14, and separator-sealer 12 all need to be modified in shape and size to conform to the different sizes and shapes of the head, neck and collar of the various types of femoral stem prosthesis. Further, the device of the present invention is not confined to use of femoral stem hip prosthesis for total hip replacement. Some patients need only the femoral head and neck to be replaced. In this cases, the head of the femoral prosthesis is inserted into the patient's existing acetabulum. In this group of prosthesis, the stem may or may not be cemented in the femoral canal. However, the present device is useful in the fixation of these prosthesis and other unfenestrated prosthesis.

As shown in FIG. 2, base guide 10 is, roughly speaking, U-shaped or horse-shoe shaped. The sides 26 and 28 at the open end 18 have wings 22 and 24 which are angulated upwardly by 41° from the horizontal sides 26 and 28 and closed end 20. The exterior surface of closed end 20, wings 22 and 24, and sides 26 and 28 may be made of material sufficiently strong to maintain its form and resist cutting and bending while at the same time being suitable for medical use. Examples are plastics and metals, particularly stainless steel. While sides 26 and 28 and closed portion 20 have the upper or superior surface containing groove 30 for the acceptance of a flange 194 (shown in FIG. 7) near the periphery of the inferior aspect or bottom of celing 14, the angulated wings 22 and 24 are not grooved. From a point 134 midway between the sides of base guide 10 at the open end thereof to the mid-point 135 of the inner aspect or inner side of closed end 20, the distance is approximately 4.3 cm. for example, for a small femur. Also, for the small femur the distance across open end 18 from point 138 to point 140 is approximately 3.2 cm. It will be evident that various sizes and right and left base guides will be sufficient to provide for different size femurs, i.e. adult, child, etc.

On the inner aspect of base guide 10 at the junction of wings 22 and 24 with horizontal sides 26 and 28, respectively, are the supports 34 and 36 which may be made of metal or plastic. The upper surface of supports 34 and 36 are on a level with the upper or superior surface of the horizontal sides 26 and 28. The inferior or bottom surfaces of supports 34 and 36 are in the same plane as the bottom or inferior surface of the corresponding abutting wings 22 and 24 and corresponding abutting horizontal sides 26 and 28. The superior or upper surfaces of supports 34 and 36 are approximately 1.2 cm. in length and 0.5 cm. in width.

An orifice 46 runs longitudinally through the bottom or inferior aspect of each support 34 and 36 for the insertion of a 0.45 Kirschner wire from the back or posterior aspect of the support. One of these "K" wires is drilled into the lesser trochanter of the femur and the other platform "K" wire pierces the closed end 20 of base guide 10 through orifice 50. The "K" wire extending through orifice 46 and the lesser trochanter of the femur may pass through the femur and pierce orifice 48 located in the closed end 20 of base guide 10. Transverse orifices 42 and 44 pass through supports 34 and 36 and the wings 22 and 24. These orifices are in straight alignment with each other and are for the insertion of a Kirschner wire, usually size 0.62 which corresponds to approximately 1/16 inch in diameter and which passes through the base guide 10 and the cortices of the femur. It is preferred to have a second set of orifices, 42A and 44A, which also pass through supports 34 and 36 and wings 22 and 24. This can be used in the event the base guide has to be realigned for proper placement of the prosthesis to permit placement of wires sufficiently distant from the openings in the bone made by the initial insertion of the wires to ensure rigid placement of the base guide.

A notch 142 is formed in the lower or posterior aspect of one side of the closed end 20 of base guide 10 for the lesser trochanter. An obligue hole 31 passes through the side 28 posterior to the notch 142 for the lesser trochanter and is directed to an oblique hole 32 located in closed end 20 lateral to the notch 142 for the lesser trochanter. These two holes 31 and 32 are for 0.62 Kirschner wires or other fixation devices such as Steinmann pins, and the like, which also pass through the cortices of the femur posterior and lateral to the lesser trochanter, respectively, and these holes are in straight alignment with each other.

The height of the wings 22 and 24 and the height of the posterior or rear aspect of the horizontal sides 26 and 28 are approximately 0.9 cm. to 1.0 cm. The horizontal sides 26 and 28 slope upwardly on their inferior or bottom surface toward the closed end 20 of base guide 10 to form a wall height of approximately 0.7 cm. at the corners of the closed end 20 of base guide 10. At the corner of closed end 20 for the lesser trochanter where notch 142 is located, the inferior or lower aspect of the corner is arched and at the apex of the arch, the wall is approximately 0.45 cm. in height.

Figure 3:
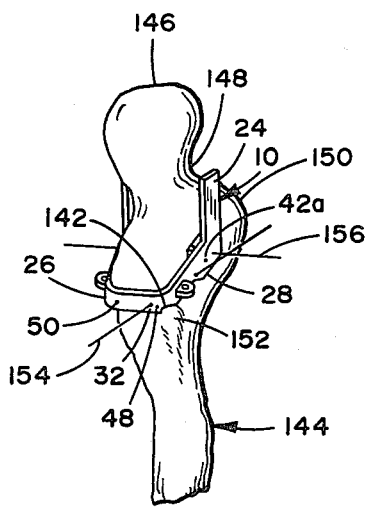
FIG. 3 is an isometric view of the base guide attached to the femur in the location of the lesser trochanter with pins extending through portions of the cortex of the femur.

FIG. 3 illustrates the attachment of the base guide 10 to the proximal end of the femur 144 prior to resection of the head and neck 148, greater trochanter 150, and lesser trochanter 152. The surgeon then positions the posterior aspect or open end of base guide 10 until the upper surfaces of sides 26 and 28 and wings 22 and 24 represent the proper slope along which the head 146 and neck 148 of femur 144 must be resected or removed. When the proper position has been determined, wire 154 is aligned with oblique holes 31 and 32 and drilled through the cortices of the femur posterior and lateral to the lesser trochanter 152 respectively. A second wire 156 is drilled through transverse holes 42 and 44, or 42A and 44A, through supports 34 and 36 and through the cortices of the femur.

Figure 4A:
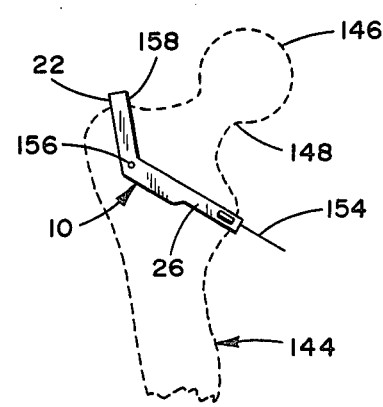
FIG. 4A is a side view of the femur having the base guide attached thereto and showing the proper angle at which the head and neck of the femur are to be resected.
Figure 4B:
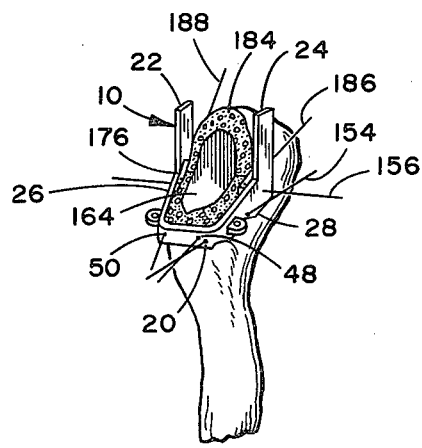
FIG. 4B is an isometric view of the femur having the head and neck thereof resected along the top edge of the wings and sides of the base guide.

The completely positioned and properly attached base guide is shown in a side view in FIG. 4A. The surgeon then utilizes a reciprocating saw to resect the head 146 and neck 148 of femur 144 by cutting along line 158 formed by the upper surface of wing 22 and side 26. If the surgeon determines that he wishes to alter the positon of the base guide 10 on femur 144 in order to change the varus or valgus of the prosthesis, he may remove pins 154 and 156 and re-insert them and repeat the cut. FIG. 4B is an isometric view of the femur after the head and neck have been resected along the top edge of the wings 22 and 24 and sides 26 and 28. The cortex 184 is exposed as well as the femoral canal 164.

Figure 5A:
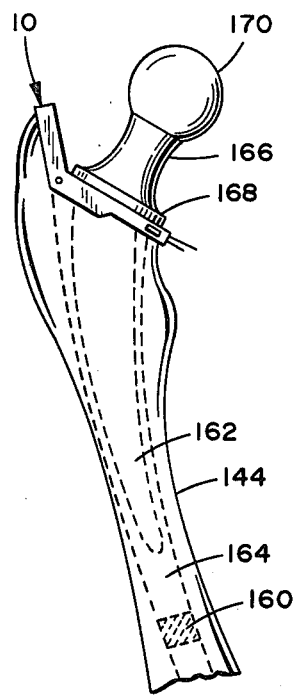
FIG. 5A is a side view of the femur after the head and neck have been resected and the femoral canal cleaned and plugged, and the stem prosthesis inserted therein.

The surgeon then prepares the femoral canal 164 in a well known manner for the insertion of the plastic or cement plug 160 which is shown in FIG. 5A. This plug is inserted approximately one inch beyond the tip of the femoral stem prosthesis 162. After the femoral canal 164 has been plugged, the femoral stem 162 is inserted into the canal 164. It may be temprarily secured to base guide 10 by means of lid clamp 16 and ceiling 14. At this point, the surgeon may take X-rays of the femoral stem prosthesis in place and determine whether this is a suitable position of the prosthesis as far as anteversion is concerned as well as determining the position of the tip of the femoral stem in the femoral canal. If the position is incorrect because of the cut made in removing the head 146 and neck 148 of the femur 144, as stated earlier, the pins may be removed and the base guide 10 re-positioned and a new cut made. Also, if the prosthesis needs to be positioned in varus or valgus, an adjustment element as shown in FIG. 8B may be placed about the neck 166 of the prosthesis and rotated until thick side 170 is in proper position to interrelate with lid clamp 16 to force the prosthesis in the proper direction.

Figure 5B:
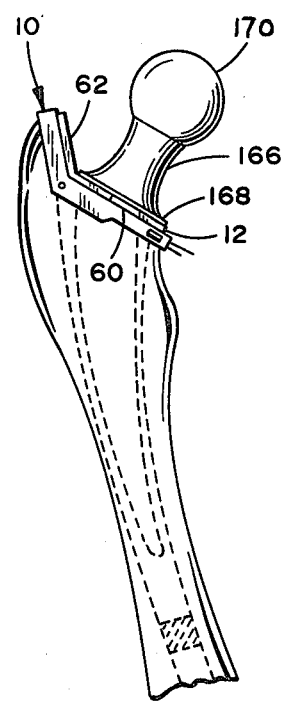
FIG. 5B is a side view of the femur similar to that shown in FIG. 5A and, in addition, illustrating the placement of the separator-sealer about the collar of the prosthesis.
Figure 6:
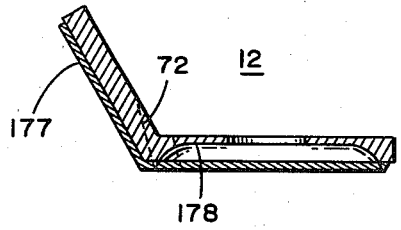
FIG. 6 is a cross-sectional view of the side of the separator-sealer illustrating the concave underside thereof.

As shown in FIG. 5B, the two pieces of separator-sealer 12 are formed from a plastic such as Isoprene and have Gelfoam 177 ironed into the inferior aspect or bottom thereof (see FIG. 6). The two pieces fit about the neck 166 and collar junction 168 of the prosthesis. The orifice 66 in separator-sealer 12 may be elliptical in shape. Several sets of separator-sealers 12 may be provided and vary from one another by having a different diameter major axis orifice direction as stated earlier. By selecting a different diameter major axis orifice direction, one can select a varying degree of anteversion of the head 170 and neck 166. While FIG. 5B shows separator-sealer 12 placed around prosthesis collar 168 and above base guide 10, in actual practice, the two selected pieces of separator-sealer 12 are separately attached to the inferior aspect or bottom of the respective halves of ceiling 14 and the combined units mounted simultaneously on the base guide 10.

Figure 5C:
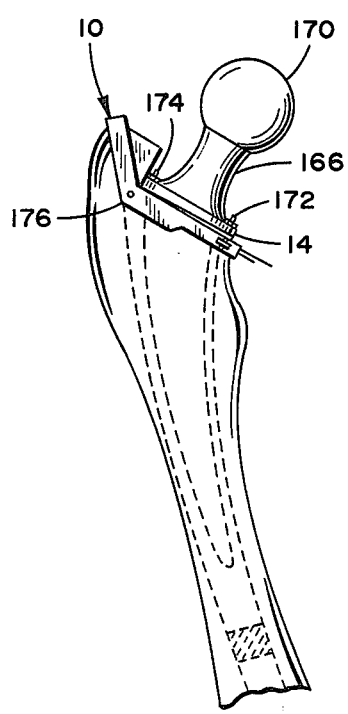
FIG. 5C is a side view of the femur as in FIG. 5B but in addition illustrating the placement of the ceiling on and above the separator-sealer and attachment to the base guide.

As can be seen in FIG. 5C, ceiling 14 is attached rigidly to base guide 10 by means of screws or bolts 172 and 174.

It is particularly important to fill in the space between the base guide 10 and the cortex at point 176 shown in FIG. 5C. Point 176 is the junction of the flat portion of ceiling 14 and the sloped portion of ceiling 14. The Isoprene forming separator-sealer 12 is molded as can be seen in FIG. 6 to have a concave surface 178 on the bottom thereof. This permits the methyl methacrylate cement being introduced through orifice 72 to cover the cut surface of the cortex and form a small exterior and superior lip on the cortex. Further, as explained earlier, the base of ceiling 14 is designed to slope slightly upwardly from the posterior to the anterior aspect. Thus, the separator-sealer 12 and the ceiling 14 do not lie directly on the cortex of the bone in the region of the calcar but do rest on the cortex at the junction of the flat portion 80 of ceiling 14 and sloped portion 96 of ceiling 14 (see FIG. 1). The purpose of having the space above the calcar is to enable the methyl methacrylate cement to cover the calcar and also to surround a portion of the collar 168 of the femoral stem prosthesis.

Figure 5D:
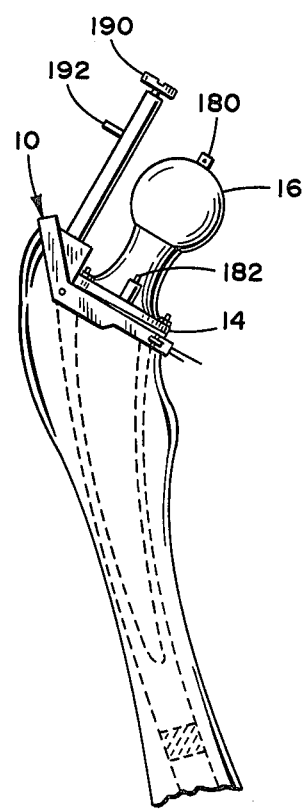
FIG. 5D is a side view of the femur as shown in FIG. 5C with the addition of the lid clamp attached to the ceiling and completely encasing the head and neck of the stem prosthesis.

Finally, the lip clamp 16 is placed over head 170 and neck 166 of the prosthesis as shown in FIG. 5D and the lid clamp is tightened together with a bolt 180 on the top thereof and then rigidly attached to ceiling 14 by means of bolts 182.

The prosthesis may now be X-rayed while in the femur prior to the insertion of the cement. After seeing the X-ray, one may alter the position of the prosthesis stem by removing the assembly from the base guide 10 and inserting an adjustment unit 168 shown in FIG. 8B about the neck 166 of the prosthesis and rotating it until thick portion 210 is either in front of, or behind prosthesis head 170 and lid clamp 116 may then be replaced and the assembly re-attached to the base guide and checked again with X-rays.

Of course, the surgeon may choose a prosthesis having a different length of neck and size of head, but in doing so, he must utilize a different size of corresponding lid clamp 16. When the surgeon is satisfied with the size of the prosthesis and its position, the lid clamp 16, ceiling 14 and separator-sealer 12 may be removed so that the prosthesis can be removed from the femoral canal and the canal cleaned, irrigated and dried.

Two small wires 186 and 188 (see FIG. 4B) are then inserted at the greater trochanter end of base guide 10 and are driven into the orifices 48 and 50 at closed end 20 of base guide 10. The purpose of these two wires is to prevent the softened Isoprene from extruding down the sides of the outer shaft of the femur between the femur 144 and the sides 26 and 28 of base guide 10.

Next, pieces of Isoprene are melted and packed between the cortex 184 and the sides 26 and 28 of the base guide and closed end 20 of base guide 10 (see FIG. 4B). The surface of the Isoprene is smoothed with a warm soldering iron tip. It is particularly important to fill in the space between the base guide 10 and the cortex 184 at the junction 176 of the flat sides of base guide 10 and sloped wings 22 and 24. The Isoprene is molded so as to permit the methyl methacrylate cement to cover the cut surface of the cortex 184 and form a small exterior and superior lip on the cortex 184. Other materials may be used as fillers in place of plastic and gelatin. For instance, a piece of silicone (Silastic) may be cut and wedged between the base guide and cortex. Silicon has the advantage of not adhering to methyl methacrylate and thus the use of gelatin is eliminated.

With the melted Isoprene placed between base guide 10 and the exterior of cortex 184 of the femur, the femoral canal is again cleansed, irrigated and dried. Pieces of Gelfoam are then ironed into the superior surface of the Isoprene which lies between base guide 10 and cortex 184. It is the Gelfoam which will later prevent the cement from adhering to the base guide 10 and lid clamp 16. Methyl methacrylate cement is then inserted into the femoral canal nearly to the surface of the cut femur.

The separator-sealer 12, ceiling 14 and lid clamp 16 are then re-attached to the base guide as shown in FIG. 5D. Additional methyl methacrylate cement is inserted in the ⅜ inch hole 98 through hose 192 under pressure with a gun (not shown) and when cement begins to exude through the ¼ inch hole 102 (shown in FIG. 1 and FIG. 7), the ¼ inch hole is plugged with a plug which is covered on the tip with Isoprene and Gelfoam or silicone to prevent cement from adhering thereto (see FIG. 9). While pressure is being maintained with the cement gun, the cement input port is sealed off by means of, for example only, plug 190 (see FIG. 10 for details). Thus the pressure provided by the cement gun has no further effect on the cement in the femoral canal and the cement gun may be removed. The cement is permitted to harden or cure. When the cement is hardened, the lid clamp 12 is removed first, then ceiling portion 14 along with separator-sealer 12 is removed. If any problem arises while attempting to remove the ceiling 14 and separator-sealer 12, water or a saline solution may be introduced into either the ⅜ inch or ¼ inch holes and separation is greatly facilitated.

Next, the two small pins 186 and 188 which lie along wings 22 and 24 of base guide 10, and which prevent the Isoprene from migrating down the sides of the femur, are removed and then the oblique pin 154 in the region of the lesser trochanter 152 is removed and finally the transverse pin 156 is removed. Of course, the previously melted Isoprene and Gelfoam are also removed. If any undesirable irregular edges of the cured methyl methacrylate cement are present, they may be easily removed by a dental burr.

Figure 7:
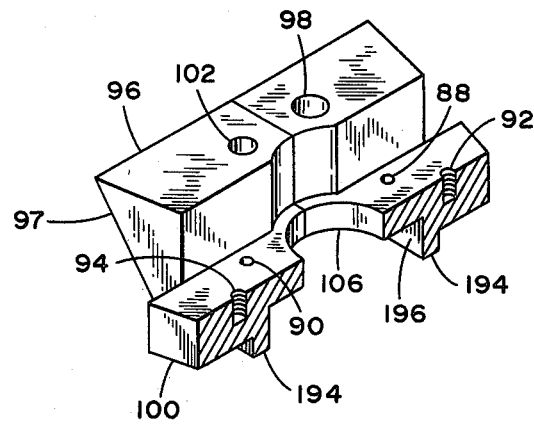
FIG. 7 is an isometric view of a cross-section of the ceiling illustrating the cement orifices as well as the orifice through which the neck of the stem prosthesis must protrude and the sealing flange on the base thereof.

FIG. 7 is an isometric view of a cross-section of the ceiling 14. In addition to the elements of ceiling 14 already disclosed in relation to FIG. 1, FIG. 7 illustrates the flange 194 which extends around the periphery of the anterior portion 80 of ceiing 14 and which mates with groove 30 on base guide 10 as illustrated in FIG. 1. Also shown in FIG. 7 is the space 196 under ceiling 14 in which separator-sealer is located when attached to base guide 10 and which allows cement to fill the space around the collar of the prosthetic device on the proper areas of the bone cortex.

Figure 8A:
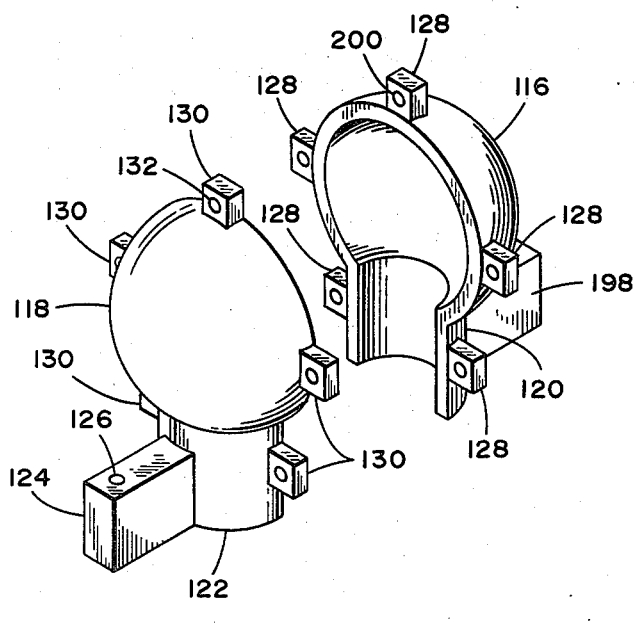
FIG. 8A is an isometric view of the two halves of the lid clamp which is utilized to enclose the head and neck of the stem prosthesis.
Figure 8B:
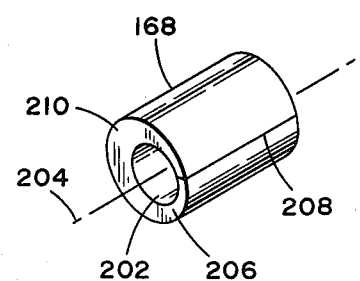
FIG. 8B is an isometric view of an adjustment unit to be positioned in the neck of said lid clamp for varying the position of the prosthesis stem in the femoral canal.

FIG. 8A is an exploded view of the two halves of the lid clamp 16. Each half, 116 and 118, has integrally formed therewith a neck 120 and 122 respectively. Also formed on the neck of each half is a support 124 and 198 respectively. As can be seen in support 124, there is an orifice 126 which may be utilized to accept a bolt or other type of fastening device in order to attach half 118 of lid clamp 16 to the ceiling 14. In like manner, support 198 has an orifice, not shown, which also accepts a bolt or fastening device to attach lid clamp half 116 to ceiling 14. Projections 128 and 130 at the top of each half contain a respective orifice 200 and 132 through which a bolt may be passed to secure the two halves 116 and 118 together.

FIG. 8B is an isometric view of the adjustment unit which may be made of a pliable material such as rubber or pliable plastic which is cylindrical in shape and which has an orifice 202 eccentrically located along a longitudinal axis 204 of said material, thereby creating a thick side 210 and a thin side 206. Further, a slit 208 extends through and along the thin side 206 whereby the adjustment unit 168 may be positioned about the neck 166 of the prosthesis and rotated to a desired location, thereby forcing the prosthesis to a fixed position when lid clamp 16 is attached to the ball and neck of the prosthesis about adjustment unit 168. It will be understood that the adjustment units will be available in different sizes and shapes including those with central orifices. Further, adjustment unit 168 may be divided into separate complimentary sections, if desired, for ease of mounting about the neck of the prosthesis.

Figure 9A:
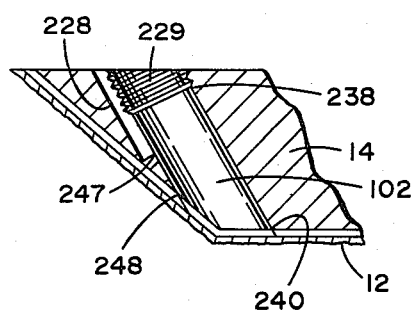
FIG. 9A is a partial cross-sectional view representing the ceiling and the separator-sealer and one of the orifices therein.
Figure 9B:
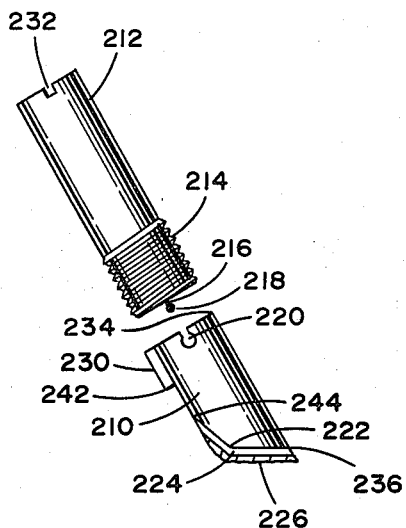
FIG. 9B is a side view of the plug used for closing the orifice shown in FIG. 9A.
Figure 9C:
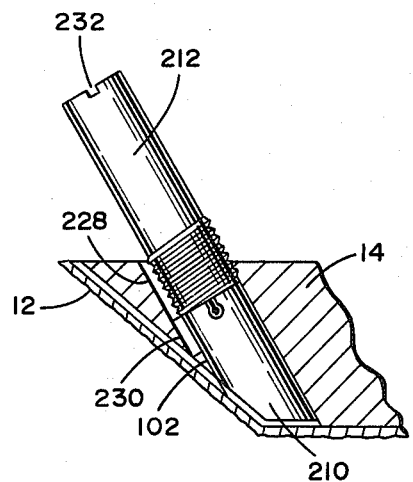
FIG. 9C is a partial cross-sectional view of the plug of FIG. 9B inserted in the orifice of FIG. 9A.

FIG. 9 has been divided into Sections A, B, and C. Section A represents the ceiling 14 and the separator-sealer 12 and shows the ¼ inch hole 102 in the ceiling 14 and separator-sealer 12. Section B shows the two sectional plugs 210 and 212 which are used to close the ¼ inch hole 102, and Section C represents the plugs 210 and 212 in place. Plugs 210 and 212 are preferably made of metal although other materials could be used. It is to be noted that plug 212 at its distal portion 214 is threaded. At the end of the plug is a narrow stem 216 and on the end of that stem is a small ball 218. This small stem 216 and ball 218 fixes into cavity 220. Stem 216 and ball 218 are slid into cavity 220 sideways and, when assembled, the entire unit can be inserted into the ¼ inch hole 102 as shown in FIG. 9C. The bottom 222 of the plug 210 is, of course, covered with Isoprene 224 and Gelfoam 226 (or silicone, not shown) as is the separator-sealer 12. In addition, it is to be noted that in the FIG. 9A, a small groove 228 is present on the posterior aspect of the ¼ inch hole 102. This groove 228 is nearly perpendicular to the horizontal portion of the ceiling 14 and separator-sealer 12. Metal ridge 230 on plug 210 slides into and mates with groove 228. It is this mechanism that prevents rotation of plug 210 as it is inserted into ¼ inch orifice 102. After inserting the plug 210 in orifice 102, compression is increased by screwing the threads of plug 212 into the threaded portion 229 of orifice 102. There is, as represented in FIG. 9C, a notch 232 at the outer end of plug 212 for the insertion of a screw driver for rapid insertion of plug 212 in orifice 102. The groove 228 not only prevents plug 210 from rotating, but it also acts as a stopper so that plug 210 is not introduced too deeply into orifice 102. Just as the distance from 234 to 236 on plug 210 must be the same distance as 238 to 240 in orifice 102, so it must be also that distances between 242 and 244 on plug 210 are exactly the same distances as between 247 and 248 associated with orifice 102.

Figure 10A:
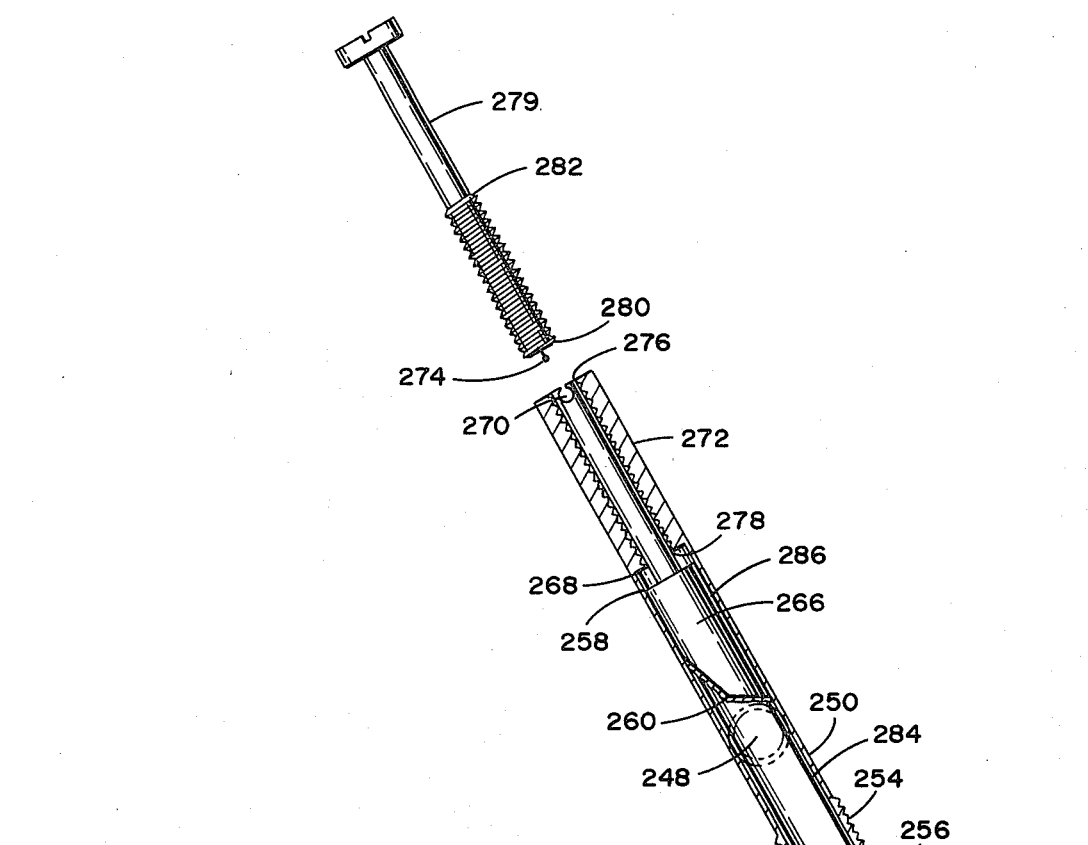
FIG. 10A is a partial cross-setional view of the filling tube for attachment of the cement syringe to the filling orifice in the ceiling.
Figure 10B:
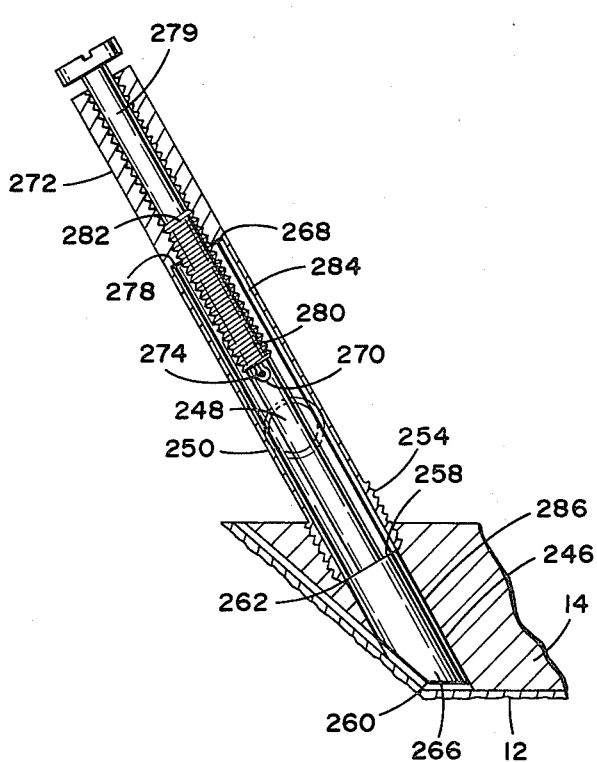
FIG. 10B is a partial cross-sectional view of the filling tube inserted in said orifice of said ceiling with a plug in place to prevent cement from escaping.

As described earlier, the ¼ inch orifice 102 is the outlet orifice in ceiling 14 for air, fluid, and excessive methyl methacrylate. The ⅜ inch orifice 246 in ceiling 14 has been described as being used for the introduction of the last portion of the needed methyl methacrylate. More specifically, this jig is not to be used for the introduction of the entire batch of methyl methacrylate into the femoral shaft. It is mandatory that the femoral shaft in the region of the distal portion of the intramedullary femoral stem be filled with methyl methacrylate with a long syringe even before the femoral stem is inserted. This jig, then, is to be used after a goodly portion of the femoral canal has been filled with methyl methacrylate. Once the femoral canal is fairly well filled, the complete jig is assembled and additional methyl methacrylate entered into the ⅜ inch orifice 246. As the methyl methyacrylate is being introduced into the ⅜ inch orifice 246 and after the air and liquid has been extruded out through the ¼ inch orifice 102, the surgeon may elect to increase the pressure for the methyl methacrylate by holding his finger over the ¼ inch orifice 102. A great deal of the pressure required will depend on the viscosity of the methyl methacrylate at the time of its introduction. It is possible in some instances to have the gun for inserting methyl methacrylate to be attached to a piece of tubing. The tubing in turn is attached to the ceiling 14 and by such mechanism the methyl methacrylate is inserted under pressure and while that pressure is being maintained, one is still able to close the ⅜ inch orifice 246. As the ⅜ inch orifice 246 is being closed, the ¼ inch orifice 102 may be opened completely or partly closed manually. FIG. 10 is a schematic representation of the device for attachment of the syringe to a filling tube and illustrating the special plug to be inserted into the ⅜ inch orifice 246. In FIG. 10A, 248 is the opening into the filling tubing for the attachment of the syringe (not shown) containing the methyl methacrylate. This opening should form the end of tubing extending outwardly a short distance from filling device 250 as an elbow for the attachment of the syringe gun, but must not extend such distance that it will not clear the lid clamp 16 as it is being screwed into the ceiling 14. As shown in FIG. 10A, the ⅜ inch orifice 246 is shown in the separator-sealer 12 and ceiling 14. The upper portion 252 of the ⅜ inch orifice 246 in the ceiling 14 is threaded. The threaded portion 254 of the filling device 250 at the lower end 256 is screwed into threaded portion 252 of ceiling 14. Again the distance from 258 to 260 must be exactly the same as the distance from 262 to 264 so that the end of the plug 266 is perfectly smooth with the under surface of the rest of the separator-sealer 12. It is to be noted that there is a portion of the filling device 250, namely between 258 and 268 which is of a greater length than the lower end of plug 266. This distance 258 to 268 permits the plug 266 to move up into the filling device 250 so that the cavity 270 in the proximal end of the plug 266 will protrude above the end of the tubing 272 to permit the ball stem mechanism 274 to be fitted into the cavity 270. Once ball stem 274 is inside cavity 270, the entire plug 266 is pushed down the tubing 272 as desired to be seated into separator-sealer 12 and ceiling 14 as illustrated in FIG. 10B. The section of the plug 266 is continuous from the top 276 down to the bottom 260. The inner aspect of the tubing 272 from 276 to 278 is threaded so that the screw portion of the plug 279 from 280 to 282 can be screwed into tubing section 272 from 276 to 278. Once the plug 266 is in place in the ceiling 14 and separator-sealer 12, as shown in FIG. 10B, then the syringe or gun containing methyl methacrylate can be removed from the opening 248 in filler device 250. Just as FIG. 9 has a groove 228 and a ridge 230 to prevent rotation of the plug 210, so must modified plug 266 also have a groove and the plunger a ridge. The groove in the tubing is represented as 284 and the ridge on the plunger as 286. In the way of further explanation and comments, particularly in regard to FIG. 10, it is conceivable that some operating surgeons will pack the femoral canal quite well with the methyl methacrylate gun, so that very little air space or liquid will be present to be squeezed out. Some operating surgeons may fill the canal to the level of the cut cortex of the femur. In some instances in which the methyl methacrylate is more free to flow, the operating surgeon may do an excellent job of packing the femoral canal so that he may elect to place the jig with the femoral stem onto the base guide and insert a small amount of methyl methacrylate into the ⅜ inch orifice 246, which would essentially eliminate all air space and liquid. However, methyl methacrylate would be under some increased pressure. In some instances, no additional methyl methacrylate needs to be inserted through opening 248. The mere advancement of the plug 266 into the ceiling 14 may well exert enough additional positive pressure without having to use the cement gun or syringe. In some instances, the ¼ inch hole 102 may be left open and become filled with methyl methacrylate which is beginning to "set-up" and become less viscous. The additional pressure applied by the plug 266, plus the fact that plug 210 must be still inserted into the ¼ inch orifice 102 may create sufficient additional pressure. It is conceivable that with the more viscous methyl methacrylate, that as one inserts the plug 210 into the ¼ inch orifice 102, one might even have to remove a portion of the methyl methacrylate in the ¼ inch orifice 102 in the ceiling 14, because as the plug 210 is driven into the ¼ inch orifice 102, it too will exert some pressure, and it is mandatory that the point 236 be smooth and on the same level as point 240. It will be noted that both the ¼ inch plug hole 102 and the ⅜ inch plug 246 are placed at a slant and this is necessary in order for the plug to rotate free of the lid clamp 16.

Thus, there has been described a novel device for facilitating the cementing of a femoral stem hip prosthesis in a prepared femoral canal. The device enables the surgeon to make the proper cut on or resection of the femoral head and neck, to properly position the prosthesis stem in the femoral canal prior to the cementing thereof, and to apply this cement to the prosthesis under pressure, thereby obviating the necessity of the surgeon attempting to manually hold the prosthesis in a rigid position until the cement sets.

In order for the present invention to be used on all sizes of femurs, it is necessary to make the base guide in varying sizes and for left and right femurs. Further, the lid clamp 16, ceiling 14 and separator-sealing 12 need to be modified in shape and size to conform to the different sizes and shapes of heads, necks and collars of the different types of prostheses. Also, if in the manufacturing of a given design and size of femoral stem hip prosth the neck and/or collar should vary in circumference of angle or size from another femoral stem hip prosthesis of supposedly the same design and size, then particular sizes of the lid clamp 16, ceiling 14 and separator-sealer 12 will need to be matched to that prosthesis to accomodate these variations and snugly fit the prosthesis. Thus, a variety of different sizes can be made available to the surgeon.

In like manner, while methyl methacrylate is a suitable bone cement, any bone cement can be used such as Howmedica's Simplex-P which is a mixture of polymethyl methacrylate and methyl methacrylate-styrene copolymer. Further, in place of Isoprene, it is possible to use any plastic or resin which does not cure or harden so rapidly so as not to give the physician ample time to properly seat the prosthesis and which plastic or resin is semi-rigid when cured or hardened and which has a low melting point. Silicone (Silastic) may be used without the gelatin cover in place of plastic or gelatin.

Some orthopedic surgeons are of the opinion that there is no need for the femoral stem prosthesis to have a collar and, in such case, they believe it is not necessary to cover the cut surface of the cortex with methyl methacrylate. This group of surgeons prefer to use a prosthesis such as the De Puy Dual-Lock prosthesis. The De Puy Dual-Lock femoral prosthesis provides dual fixation by self-locking of the largest possible stem into the medial/lateral aspect of the medullary cavity and by such a stem, the surgeon determines the varus or valgus and the anteversion of his choice. Usually, when a femoral stem prosthesis without a collar is used, the neck of the patient's femur is resected higher than illustrated in FIG. 4 of the drawings. The prosthetic device and system will provide increased pressure of the cement as already described herein; however, the sequence of the use of the base guide, separator-sealer, ceiling, and lid clamp are alternated as described below.

Figure 11:
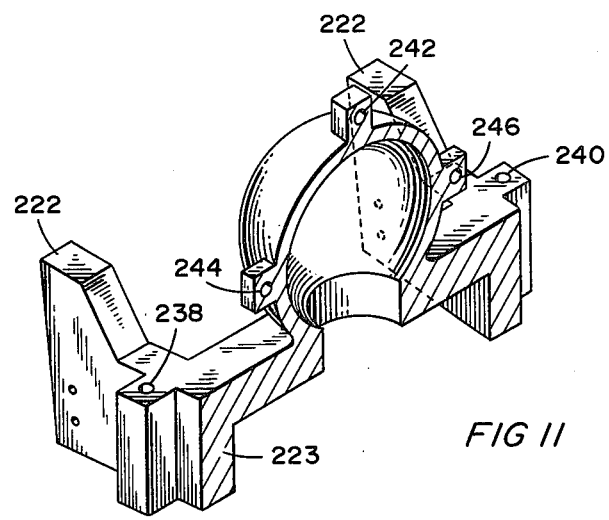
FIG. 11 is a cross-sectional view of a lid clamp guide.

When using a collarless prosthesis, the ceiling presses the separator-sealer securely against the cut cortex 184 of the femur. There is no need to "putty" rubberoid plastic between the base guide and the cortex of the femur, as previously discussed with relation to FIG. 4B. The separator-sealer, in the case of both collarless prosthetic devices and such devices with a collar as described earlier, may be plastic and gelatin or a rubberized product or silicone such as Silastic which is a trade name of Dow Corning Corp. A lid clamp guide 220 is divided into anterior and posterior "halves" as shown in FIG. 11 similar to the separator-sealers illustrated in FIG. 1 for the purpose of assembling and dissembling it about the head and neck of the prosthesis. It is used, in this case, to position the base guide 224. Because the operating surgeon determines the position of the prosthesis, the collarless prosthetic device is amenable to the surgeon's choice of position by locating the lid clamp guide 220 and then positioning the base guide 224 shown in FIG. 12 according to the "dictates" of the position of the lid clamp guide 220.

The lid clamp guide 220 fits snugly about the superior half of the prosthesis head and only a small portion of the middle and lower portion of the neck of the prosthesis. it also extends laterally, medially, anteriorly, and posteriorly, but as it approaches the greater trochanter, a void is present in the area of the sloped portion of the lid clamp guide 220 as shown in FIG. 11. Only wings 222 remain as a guide for positioning the base guide 224 illustrated in FIG. 12. The "void" allows the lid clamp guide to fit about the region of the greater trochanter before the final bone cut is made. Lid clamp guides may be built with or without voids. In some instances, the operating surgeon, when provided with a thick separator-sealer, may choose to insert the separator-sealer under the surface of a lid clamp guide which does not have a void. Thus, the lid clamp guide without the void is used with a thick separator-sealer as the final assembly when the cement is inserted under pressure.

Lid clamp guide 220 also has a "ceiling" portion 223 integrally formed with the lid clamp for enabling the base guide to be attached thereto, after correct positioning, by means of bolts or the like through bolt holes 238 and 240. The temporary fixation of the lid clamp guide is accomplished by inserting "K" wires through orifices 261 and/or 262, the cortices of the femur and then corresponding orifices in the other wing 222. If insertion of "K" wires becomes a problem, the base guide may be secured with two small, flexible drill bits which may be drilled through the plastic base guide and through the cortices of the femur and the drill bits left in place as fixation until the prosthetic device is ready to be removed in its entirety.

Figure 12:
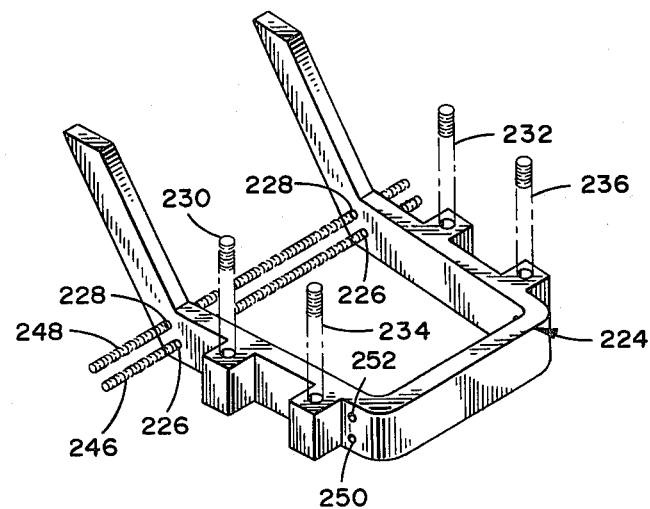
FIG. 12 illustrates an alternate base guide.
Figure 13:
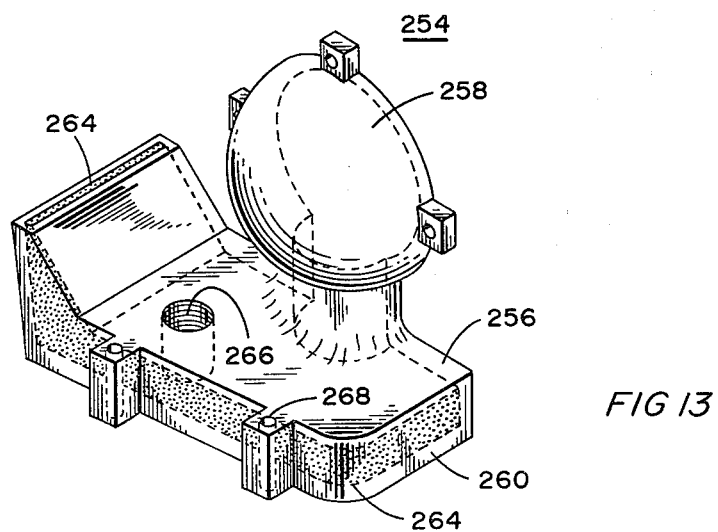
FIG. 13 illustrates one-half of an alternate ceiling-lid clamp.

After the head and neck of the patient's femur has been exposed and the head of the femur dislocated from the acetabulum, the head and the small portion of the neck of the patient's femur is removed by a saw as indicated previously. The line of dissection of the neck of the femur is slightly higher than the anticipated final dissection. The femoral awl reamer is then used to ream the medullary canal of the femur and other reamers are used to prepare the femoral canal for the collarless femoral stem prosthesis and the distal bone plug or the distal cement plug. A trial positioning of the components is used to provide assessment of the femoral shaft preparation. The medullary canal is first irrigated and dried, and the distal bone plug or cement plug placed in the femoral canal at a point beyond that which the stem prosthesis will reach and the trial prosthesis is then tapped into place in the desired varus or valgus and anteversion position. The lid clamp guide 220 which fits over and around the remaining part of the neck of the patient's femur is then secured to the head and neck of the trial prosthesis by bolts through orifices 242, 244, and 246 without disturbing the desired position of the trial prosthesis. The desired rotation of the lid clamp guide 220 is determined before final securing of the lid clamp guide 220 to the trial prosthesis. Because of the snug fit of the lid clamp guide 220 to the trial prosthesis, no adjustment unit, as shown in FIG. 8B, is needed. After the lid clamp guide 220 is secured to the trial prosthesis, the properly positioned base guide 224 shown in FIG. 12 is secured to the lid clamp guide 220. The base guide 224 is then secured to the neck of the femur by two Kirschner wires or pins which pass through the holes 226 and 228 of the base guide and the cortices of the femur. These wires or pins may be threaded as at 246 and 248 to receive locking nuts which may be used if desired. Further, orifices 250 and 252 may receive additional threaded Kirschner wires if desired. The lid clamp guide 220 and the trial prosthesis are then removed from the femur, leaving the base guide 224 attached to the femur. The femoral neck is then cut with a saw as directed by the position of the base guide 224 shown in FIG. 12. At this time, if the area about the greater trochanter has been destroyed such that a tight seal will not be provided between the cortex of the greater trochanter and the separator-sealer, then a small amount of methyl methacrylate, usually from the same batch-mix as was used for the distal femoral plug, should be molded or pressed into these defects digitally. In some instances, it may be necessary to cover the medullary surface which is to receive this methyl methacrylate with absorbable gelatin or Silastic strips which may be used as a filler between the base guide 224 and the cortex and then one assembles and positions the trial prosthesis and ceiling lid clamp 254 (one-half of which is shown in FIG. 13) to assure that the permanent femoral stem prosthesis has adequate space or clearance for its insertion. Ceiling lid clamp 254 has a ceiling portion 256 and a lid clamp portion 258. Ceiling portion 256 has a flange 260 on the inferior or bottom surface thereof. Its function is to contain the separator-sealer 264 when attached to the base guide 224. Also, the lid clamp portion 258 has orifice 266 for receiving the cement gun as set forth herein with respect to the previous embodiment. The other half of the ceiling lid clamp 254 has the orifice for the pressure plug. Both orifices are used as has previously been explained.

At such time when the distal plug is hardened and the neck and greater trochanteric area are cut and fitted for the ceiling lid clamp 254 and permanent attachment of the collarless prosthesis, then the femoral canal is again irrigated and dried and methyl methacrylate is introduced with a gun into the canal. The prosthesis ceiling lid clamp 254 and separator-sealer are then secured to the base guide 224 by means of bolts 230, 232, 234, and 236 which are inserted in orifices such as 268. Additional methyl methacrylate is then pressurized with a gun and the connector attachment through the larger hole 266 in the ceiling lid clamp 254 and separator-sealer as indicated previously. The gun is detached after the larger hole 266 in the ceiling-lid clamp is closed and the smaller hole closed with its plug in accordance with the estimated time and amount of pressure desired all as previously described. After the cement sets, the base guide 224 and ceiling lid clamp 254 cam be removed and the operation completed.

While the invention has been described in connection with a preferred embodiment, it is not intended to limit the scope of the invention to the particular form set forth, but, on the contrary, it is intended to cover such alternatives, modifications, and equivalents as may be included within the spirit and scope of the invention as defined by the appended claims.

What is claimed is:

1. A device for cementing a femoral stem hip prosthesis having a head, neck, collar and stem in a prepared femoral canal comprising:
    (a) means for mounting said femoral stem of said prosthesis in said femoral canal in a rigid relationship, and
    (b) means independent of said prosthesis and coupled to said mounting means for introducing cement into said canal about the periphery of said stem for cementing said prosthesis stem in said canal while in said right relationship whereby a strong bond is obtained between said prosthesis stem and said femur.

2. A device as in claim 1 wherein said cementing means comprises:
    (a) means for applying said cement to said prepared femoral canal under pressure, and
    (b) means for maintaining said pressure until said cement hardens about said prosthesis stem.

3. A device as in claim 1 wherein said mounting means comprises:
    (a) a base guide adapted to be rigidly attached to the proximal end of said femur as a guide for removing the neck of said femur to expose the femoral calcar and canal, and
    (b) a lid clamp for rigidly securing the femoral stem to said base guide.

4. A device as in claim 3 wherein said base guide comprises:
    (a) a generally U-shaped attachment with the open end of said U being wider than the closed end,
    (b) a wing extending upwardly and outwardly from the outer end of each arm of said U, and
    (c) at least one pair of orifices on said U-shaped attachment in spaced relationship for allowing a pin to be inserted through the cortex of said femur when said pin is inserted from one orifice to the other, thereby rigidly fastening said attachment to said femur.

5. A device as in claim 4 wherein said closed end of said U-shaped attachment is adapted to be held snugly against or near the lesser trochanter of said femur.

6. A device as in claim 5 wherein said closed end of said U-shaped attachment is notched for the lesser trochanter to allow a snug fit.

7. A device as in claim 6 further including means on said base guide for rigidly securing said lid clamp to said base guide.

8. A device as in claim 3 wherein said means for applying said cement to said femoral canal comprises:
   (a) a separator-sealer device having first and second orifices therein for operable contact with said femoral canal and mounted about the neck and collar junction of said prosthesis for providing a seal around the collar of said prosthesis and over the calcar of said femur,
   (b) a ceiling mounted above said separator-sealer and rigidly attached to said base guide, said ceiling having first and second orifices super-imposed over the abutting corresponding ones of said first and second orifices of said separator-sealer, said first orifice providing a means for inserting cement under pressure into said femoral canal, around said prosthesis collar and over said femoral calcar and said second orifice providing an air vent to allow air displaced by said cement to leave said canal,
   (c) said lid clamp enclosing said femoral prosthesis head, and
   (d) means on said ceiling for enabling said lid clamp to be rigidly attached thereto whereby said femoral stem prosthesis is held rigidly in place while said cement is applied to and hardens in said femoral canal, around said prosthesis collar and over said femoral calcar.

9. A device as in claim 8 wherein said separator-sealer is smaller than and fits within said base guide.

10. A device as in claim 9 wherein said separator-sealer comprises:
    (a) a plastic body having a concave inferior surface whereby it rests on said femur only on the outer edges of said plastic whereby said cement can cover the femoral calcar and surround the collar of said femoral stem prosthesis, and
    (b) an absorbable component applied to said inferior surface to prevent said separator-sealer from being cemented to said femur.

11. A device as in claim 10 wherein said plastic is semi-rigid when cured or hardened, has a low melting point, and does not cure or harden rapidly.

12. A device as in claim 9 wherein said base guide includes a groove around the upper edge of the U-shaped portion thereof.

13. A device as in claim 12 wherein:
    (a) said ceiling is larger than said U-shaped portion of said base guide, and
    (b) a flange extends downwardly about the periphery of the underside of said ceiling, said flange being superimposed over the coextensive with said groove in said base guide whereby said groove and flange form a seal to prevent said cement from escaping.

14. A device as in claim 13 wherein said cement is methyl methacrylate.

15. A device as in claim 14 wherein said separator-sealer, said ceiling and said lid clamp are formed from opposed complimentary sections thereby allowing them to be placed around said stem prosthesis from each side thereof.

16. A device as in claim 8 further including:
    (a) an ajustment unit for varying the position of said prosthetic stem in said canal, said adjustment unit comprising:
       (i) a pliable material cylindrical in shape,
       (ii) an orifice eccentrically located along a longitudinal axis of said material thus creating a thick side and a thin side, and
       (iii) a slit extending through and along said thin side whereby said material may be positioned about the neck of said prosthesis and rotated to a desired location thereby forcing said prosthesis to a fixed position when said lid clamp is attached thereto.

17. A device as in claim 16 wherein said adjustment unit is formed in two complimentary sections for ease of mounting about the neck of said prosthesis.

18. A method of cementing a femoral stem hip prosthesis in a prepared femoral canal, said prosthesis comprising a head, neck, and stem, said method comprising the steps of:
    (a) inserting the stem of said prosthesis in said prepared femoral canal,
    (b) attaching said prosthesis to said femur in a rigid relationship, and
    (c) introducing cement into said canal independent of said prosthesis and about the periphery of said stem for cementing said prosthesis stem in said canal while said prosthesis is maintained in said rigid relationship.

19. A method as in claim 18 wherein the step of attaching said prosthesis to said femur in a rigid relationship further comprises the steps of:
    (a) fastening a base guide to the proximal end of said femur in a fixed relationship,
    (b) resecting the neck of said femur along a line defined by said base guide to expose the femoral calcar and canal,
    (c) cleaning said femoral canal,
    (d) inserting said prosthesis stem in said canal in a desired position, and
    (e) rigidly securing said prosthesis to said base guide.

20. A method as in claim 19 further comprising the steps of:
    (a) X-raying said inserted prosthesis to determine the correct position thereof,
    (b) repeating steps (d) and (e) until the X-ray reveals said prosthesis to be in the correct position in said canal, and
    (c) applying cement to said femoral canal under pressure.

21. A method as in claim 20 wherein the step of rigidly securing said prosthesis to said base guide comprises the steps of:
    (a) enclosing said prosthesis head with a lid clamp, and
    (b) rigidly attaching said lid clamp to said base guide to hold said prosthesis in a rigid position.

22. A method as in claim 21 further including the steps of:
    (a) forming an adjustment unit from a cylindrical shaped, pliable material,
    (b) locating an orifice eccentrically along a longitudinal axis of said cylindrical shaped material thereby creating a thin side and a thick side, and (c) forming a slit extending through and along the length of the thin side of said material whereby said material may be positioned as desired about the neck of said prosthesis and between the neck and lid clamp whereby the prosthesis is positioned as desired in said canal.

23. A method as in claim 22 wherein the step of applying said cement to said femoral canal under pressure further comprises the steps of:
   (a) mounting a separator-sealer about the prosthesis neck and collar junction, said sealer having first and second orifices in operative contact with said femoral canal,
   (b) mounting a ceiling above said separator-sealer, said ceiling having first and second orifices superimposed over and abutting corresponding ones of said first and second orifices of said separator-sealer, and a third orifice through which the neck of said prosthesis passes,
   (c) rigidly securing said ceiling to said base guide,
   (d) rigidly securing said lid clamp to said ceiling whereby said prosthesis is fixedly located with respect to said femoral canal,
   (e) applying cement to said first orifice of said ceiling under pressure whereby said cement enters said femoral canal about said prosthesis stem, around said prosthesis collar, and over said femoral calcar, said cement being applied under pressure until the cement begins to flow from said second orifice, and
   (f) closing said second orifice and maintaining said pressure until said cement hardens in said femoral canal about said prosthesis stem.

24. A method as in claim 23 further comprising the steps of:
   (a) forming said separator-sealer of plastic,
   (b) adding an absorbable component on the underside thereof, and
   (c) shaping said plastic with a concave underside whereby it rests on said femur only on the outer edges of said plastic whereby said cement can cover the femoral calcar and surround the collar of said femoral stem prosthesis.

25. A method as in claim 24 further comprising the step of utilizing methyl methacrylate as said cement.

26. A method as in claim 25 further comprising the step of forming said separator-sealer, said ceiling and said lid clamp with opposed complimentary sections which may be placed about said stem prosthesis from opposite sides thereof.

27. A method as in claim 24 further including the step of sealing any space between said base guide and said femur with a malleable material to prevent said cement from adhering to said base guide and the outside of said femur.

28. A device for cementing a collarless femoral stem hip prosthesis having a head, neck and stem in a prepared femoral canal of a femur wherein a portion of the head and neck of said femur has been removed comprising:
   (a) means for mounting the stem of said collarless prosthesis rigidly in said femoral canal in the correct position for final use, and
   (a) means coupled to said mounting means independent of said prosthesis for introducing cement into said canal about the periphery of said stem for cementing said collarless prosthesis in said canal in said rigid position whereby a strong bond is obtained between said prosthesis and said femur.

29. A device as in claim 28 wherein said mounting means comprises:
   (a) a lid clamp guide attached to said collarless femoral stem hip prosthesis while said prosthesis is correctly positioned in said femoral canal,
   (b) a base guide rigidly attached to said lid clamp guide whereby said base guide may be correctly positioned, and
   (c) means for fixedly attaching said base guide in its correct position to the proximal end of said femur whereby said lid clamp guide may be removed and the remaining head and neck of said femur is resected using said base guide as a reference.

30. A device as in claim 29 wherein said lid clamp guide comprises:
   (a) a ceiling portion for correctly positioning said base guide,
   (b) a clamp integrally formed with said ceiling portion for snugly fitting about the head and a portion of the neck of said prosthesis, and
   (c) opposed complimentary sections forming said ceiling portions and clamp thereby allowing said lid clamp guide to be placed around said stem prosthesis head and neck from opposite sides.

31. A device as in claim 30 wherein said means for fixedly attaching said base guide to said proximal end of said femur in its correct position comprises:
   (a) a base guide having a U-shaped frame,
   (b) at least one orifice in each leg of said U-shaped frame,
   (c) a pin threaded on each end and inserted from one orifice in one of said legs and adapted to pass through said femur and the other orifice in said other leg, and
   (d) nuts tightened on said threads on each end of said pin whereby said base guide is adapted to be attached to said femur in a rigid relationship.

32. A device as in claim 31 further including:
   (a) a plurality of orifices in each of said legs of said U-shaped frame, and
   (b) a like plurality of threaded pins whereby each pin may pass from one orifice in one leg through said femur and a corresponding orifice in said other leg to hold said base guide in said rigid relationship to said femur.

33. A method of cementing a collarless femoral stem hip prosthesis having a head, neck and stem in a prepared femoral canal wherein a portion of the head and neck of said femur has been removed comprising:
   (a) inserting the stem of said prosthesis in said prepared femoral canal,
   (b) attaching a lid clamp guide to said prosthesis head,
   (c) positioning said lid clamp guide in its correct location,
   (d) attaching a base guide to said correctly positioned lid clamp guide,
   (e) rigidly attaching said correctly positioned base guide to said femur,
   (f) removing said lid clamp guide and said prosthesis,
   (g) resecting the remaining head and neck of said femur using said base guide as a reference,
   (h) re-inserting said collarless prosthesis stem in said prepared femoral canal,
   (i) attaching a ceiling-lid clamp to said prosthesis head and said base guide in a rigid relationship to form a cement tight seal, and (j) cementing said collarless prosthesis stem in said canal while said prosthesis is maintained in said rigid relationship.

34. A method as in claim 33 further including the steps of:

(a) providing an orifice in said ceiling-lid clamp, and
(b) introducing said cement into said femoral canal and under said ceiling-lid clamp through said orifice under pressure.

* * * * *

UNITED STATES PATENT AND TRADEMARK OFFICE
CERTIFICATE OF CORRECTION

PATENT NO. : 4,357,716
DATED : November 9, 1982
INVENTOR(S) : Byron L. Brown

It is certified that error appears in the above-identified patent and that said Letters Patent are hereby corrected as shown below:

Column 5, line 66, "setional" should be --sectional--.

Column 7, line 65, "porton" should be --portion--.

Column 8, line 31, "e" should be --be--.

Column 10, line 35, "temprarily" should be --temporarily--.

Column 15, line 47, "prosth" should be --prosthesis--.

Column 18, line 20, "cam" should be --can--.

Column 18, line 40, "right" should be --rigid--.

Column 20, line 4, "ajustment" should be --adjustment--.

Column 21, line 63, "(a)" should be --(b)--.

Signed and Sealed this

First Day of March 1983

[SEAL]

Attest:

GERALD J. MOSSINGHOFF

Attesting Officer

Commissioner of Patents and Trademarks